United States Patent [19]
Gelsinger

[11] Patent Number: 5,683,491
[45] Date of Patent: Nov. 4, 1997

[54] METHOD FOR DETERMINING SATURATION OF CARBON FILTERS IN A GAS TREATMENT PROCESS

[75] Inventor: James Owen Gelsinger, Mobile, Ala.

[73] Assignee: Mobil Oil Corporation, Fairfax, Va.

[21] Appl. No.: 633,270

[22] Filed: Apr. 16, 1996

[51] Int. Cl.$^6$ .............. B01D 15/08; B01D 53/14
[52] U.S. Cl. .............. 95/82; 95/235; 95/236; 423/228
[58] Field of Search .............. 55/270; 95/8, 11, 95/82, 235, 236; 423/220, 228, 229

[56] References Cited

U.S. PATENT DOCUMENTS

| | | | |
|---|---|---|---|
| 3,009,864 | 11/1961 | Webb | 95/8 |
| 3,208,230 | 9/1965 | Fourroux | 95/8 X |
| 3,284,162 | 11/1966 | Deal et al. . | |
| 3,347,621 | 10/1967 | Papadopoulos et al. . | |
| 3,352,631 | 11/1967 | Zarker . | |
| 3,376,356 | 4/1968 | Freitas et al. . | |
| 3,463,603 | 8/1969 | Freitas et al. . | |
| 3,559,455 | 2/1971 | Karasek | 73/23.1 |
| 4,545,965 | 10/1985 | Gazzi et al. | 95/235 X |
| 4,671,103 | 6/1987 | Dickakian | 73/61.1 C |
| 5,108,466 | 4/1992 | Klein et al. | 95/8 X |
| 5,437,179 | 8/1995 | Wegand et al. | 73/23.35 |

FOREIGN PATENT DOCUMENTS

| | | | |
|---|---|---|---|
| 3400133 | 7/1985 | Germany | 95/8 |

*Primary Examiner*—Robert Spitzer
*Attorney, Agent, or Firm*—Malcolm D. Keen

[57] ABSTRACT

A method for determining the efficiency of a carbon filter to absorb hydrocarbons from an organic amine solvent. After the solvent has passed through the filter, a sample is taken and passed through a standard gas chromatograph (GC) to measure the area counts for the hydrocarbons and the solvent. The sample does not have to have an internal standard added thereto nor does it have to be measured before it is run through the GC. The area counts are converted into actual amounts by using Reduction Factors taken from a specially-prepared calibration table. These amounts are normalized and added to give the total amount of hydrocarbons present in the solvent after it has passed through the carbon filter.

16 Claims, 2 Drawing Sheets

METHOD FOR DETERMINING SATURATION OF CARBON FILTERS IN A GAS TREATMENT PROCESS

DESCRIPTION

1. Technical Field

The present invention relates to a method for determining the saturation of carbon filters in a gas treatment process and in one of its aspects relates to a method whereby the hydrocarbon content of a regenerated solvent used in extracting acid gases from a hydrocarbon gas stream is measured by an expedient gas chromatography technique after said solvent has passed through a carbon filter to thereby determine the absorption efficiency of the filters at any given time.

2. Background

It is well known that many hydrocarbon gas streams (i.e. "sour gas") produced from certain subterranean formations contain substantial volumes of "acid gases" (e.g. hydrogen sulfide, carbon dioxide, and the like) which must be substantially removed from the gas before it can be passed on to market. One known process for treating a "sour gas" stream involves contacting the gas stream in a contactor vessel with a liquid solvent (e.g. organic amines, such as methyldiethanolamine (MDEA) and other additives). The solvent has the capacity to absorb the acid gases and carry them out of the gas stream. After the acid gases have been removed or reduced to acceptable levels by the solvent, the treated hydrocarbon gas stream is passed on for use or to market.

The "rich" solvent (i.e. the solvent plus the acid gases) passes from the contactor vessel to a regenerator vessel where the acid gases are separated from the solvent. The separated acid gases are then passed on for further processing while the regenerated solvent is recycled for use in the solvent contactor vessel.

Unfortunately, as the amine solvents absorb the acid gases from the gas stream, they also solublize and pick up small amounts of the liquid hydrocarbons from the stream. When the "rich solvent" is regenerated, a substantial amount of these solubized hydrocarbons remain in the solvent. This build up of hydrocarbons in the recycled solvent has several negative effects on the gas treating process. For example, e.g. increased hydrocarbons in the recycled solvent can cause an increase in the liquid hydrocarbon concentration of the acid gases which pass from the solvent regenerator to a Sulfur Recovery Unit (SRU), e.g. a Claus Unit, thereby reducing the efficiency of converting the hydrogen sulfide ($H_2S$) in the acid gas to sulfur.

Further, the hydrocarbon buildup in the recycled solvent can increase the probability of foaming in the primary amine absorption process (i.e. in the contactor vessel) which can lead to excess slugging of acid gases to the SRU and reduced absorption capacity of the solvent, itself. Acid gas slugging, in turn, increases sulfur dioxide emissions from the process while the reduced absorption capacity will cause reduced sales gas production and/or cause the overall gas treatment process to "sour up".

One known technique for reducing or delaying the buildup of hydrocarbons in the recycled solvent is to pass a portion (i.e. slip stream) of the regenerated solvent through a carbon filter(s) before it is returned to the contactor vessel. The carbon filter(s) absorbs the liquid hydrocarbons from the slip stream of the recycled solvent with the filtered solvent then being recombined with the main stream of recycled solvent before the regenerated solvent passes back through the contactor. It has been found that by treating only a portion of the regenerated solvent, the hydrocarbon contamination in the filters can be kept at manageable levels, thereby alleviating substantially all of the negative side-effects caused by the hydrocarbon content of the regenerated solvent.

As will all filters, the carbon will eventually become loaded (i.e. saturated) with the hydrocarbons to a point where its effectiveness in controlling the hydrocarbon buildup in the solvent is lost. If the carbon is not replaced before it becomes saturated to this point, the hydrocarbons in the regenerated solvent will not be removed by the filter but will pass therethrough thereby resulting in the negative side-effects (e.g. foaming in the contactor) discussed above.

Presently, there is no known way to measure the hydrocarbon loading (i.e. saturation) on the carbon filter(s) on a prescribed basis (e.g. daily) whereby the filter(s) can be monitored and changed before the hydrocarbon saturation exceeds the effective capacity of the filter. Again, if the carbon is not timely replaced, the gas treatment process may have to be shut down to correct the resulting side-effects. This may seriously affect the overall economics of the treating process.

In presently-known gas treating processes of this type which use amine solvents, the condition of the filter(s) is loosely monitored by measuring the differential pressure across the filter. An increase in differential pressure will occur when the flow through the filter becomes partially restricted, thereby indicating that the absorption capacity of the filter has been reached. The carbon is then changed, but by this time it may be too late to prevent foaming in the contactor which, in turn, may require shutting in the process until the situation has been corrected. Accordingly, there appears to be a need for a way to measure the effectiveness of the carbon filters at any time during the gas treatment process so that the carbon can be changed before the buildup of hydrocarbons in the regenerated solvent exceeds that which produces foaming in the contactor.

SUMMARY OF THE INVENTION

The present invention provides a method for treating a sour hydrocarbon gas stream to remove acid gases (e.g. $H_2S$ and/or $CO_2$) from said gas stream by contacting said stream with a solvent (e.g. an organic amine such as "Sulfinol" which is comprised of Sulfolane (cyclo-tetramethylene sulfone) and MDEA (methyldiethanolamine)). The rich solvent is regenerated by removing the acid gases and is then recycled for further use in removing acid gases from the sour gas stream. As the regenerated solvent is recycled, at least a portion of the regenerated solvent (i.e. a side stream) is passed through a carbon filter(s) to remove those hydrocarbons which had been absorbed from the sour gas stream into the solvent along with the acid gases.

In carrying out the present invention, a method is provided for determining, at any given time, the absorption efficiency of the carbon filter (i.e. the ability of the carbon to absorb the hydrocarbons from the regenerated solvent). That is, the saturation of the carbon filter can be determined at any given time. Basically, this is done by taking a sample of said regenerated solvent after it has passed through said carbon filter and passing it through a standard gas chromatograph (GC) to provide a chromatogram on which the relative area counts for the known hydrocarbons and the solvent are recorded.

The measured area counts for each of the particular components are then converted into corresponding actual amounts by using predetermined, reference values (i.e. Reduction Factors) taken from a specially-prepared calibration table. The amounts of the individual hydrocarbon components are then added to produce the total amount of hydrocarbon which is present in said regenerated solvent after it has passed through said carbon filter.

By taking samples of the filtered, regenerated solvent at regular intervals (daily), the actual saturation of the filter can be readily monitored. When the total amount of hydrocarbons in the filtered solvent approaches an unacceptable level (e.g. 1.5%, by volume), the filter will have lost its ability to remove sufficient hydrocarbons from the regenerated solvent. The carbon can then be replaced before the contaminated solvent can cause any of the adverse side-effects normally associated therewith.

More specifically, in carrying out the present method, a special calibration table is first compiled by passing a test sample of known composition through the GC. The test sample is comprised of (a) a known volume of the particular solvent used in process and (b) a known volume of the actual hydrocarbons which will be present in the particular hydrocarbon gas stream to be treated. The resulting chromatogram is analyzed and the "reduction factors" (RF) for each of the hydrocarbon components in the test sample are calculated either by using standard GC techniques or, preferably, by using a known and well accepted theoretical relationship. The RF(s) for the solvent is determined by manual, forced-fit analysis wherein values for the solvent are assumed and then adjusted to match the measured area counts from those peaks on the chromatogram which correspond to the solvent.

After the calibration table has been compiled, an actual sample of regenerated solvent is taken downstream of the carbon filter and is run through the GC. The respective RFs from the calibration table are then used to convert the area counts of respective hydrocarbons to their respective actual amounts in the sample. These amounts are then added to arrive at the total amount of contaminating hydrocarbon present in the filtered solvent at the time the sample was taken. It can be seen that with this procedure, the saturation of the carbon filters can be monitored at any time during the gas treatment process by merely taking a sample of the filtered solvent and processing it through a GC as described above.

The gas chromatography method of the present invention differs from known GC methods in that it does not require an internal standard to be added to each sample before the sample is run through the GC nor does it require that the volume of the sample be accurately measured as is required with known prior GC procedures. Accordingly, by using the special calibration table of RFs compiled in accordance with the present invention, the use of internal standards and elaborate calibration and sample preparation and careful measurements are eliminated. This allows the saturation of the carbon filters to be monitored at any given time with a minimum effort and without requiring an experienced GC operator.

BRIEF DESCRIPTION OF THE DRAWINGS

The actual construction, operation, and apparent advantages of the present invention will be better understood by referring to the drawings which are not necessarily to scale and in which like numerals identify like parts and in which.

BEST KNOWN MODE FOR CARRYING OUT THE INVENTION

Figure 1:
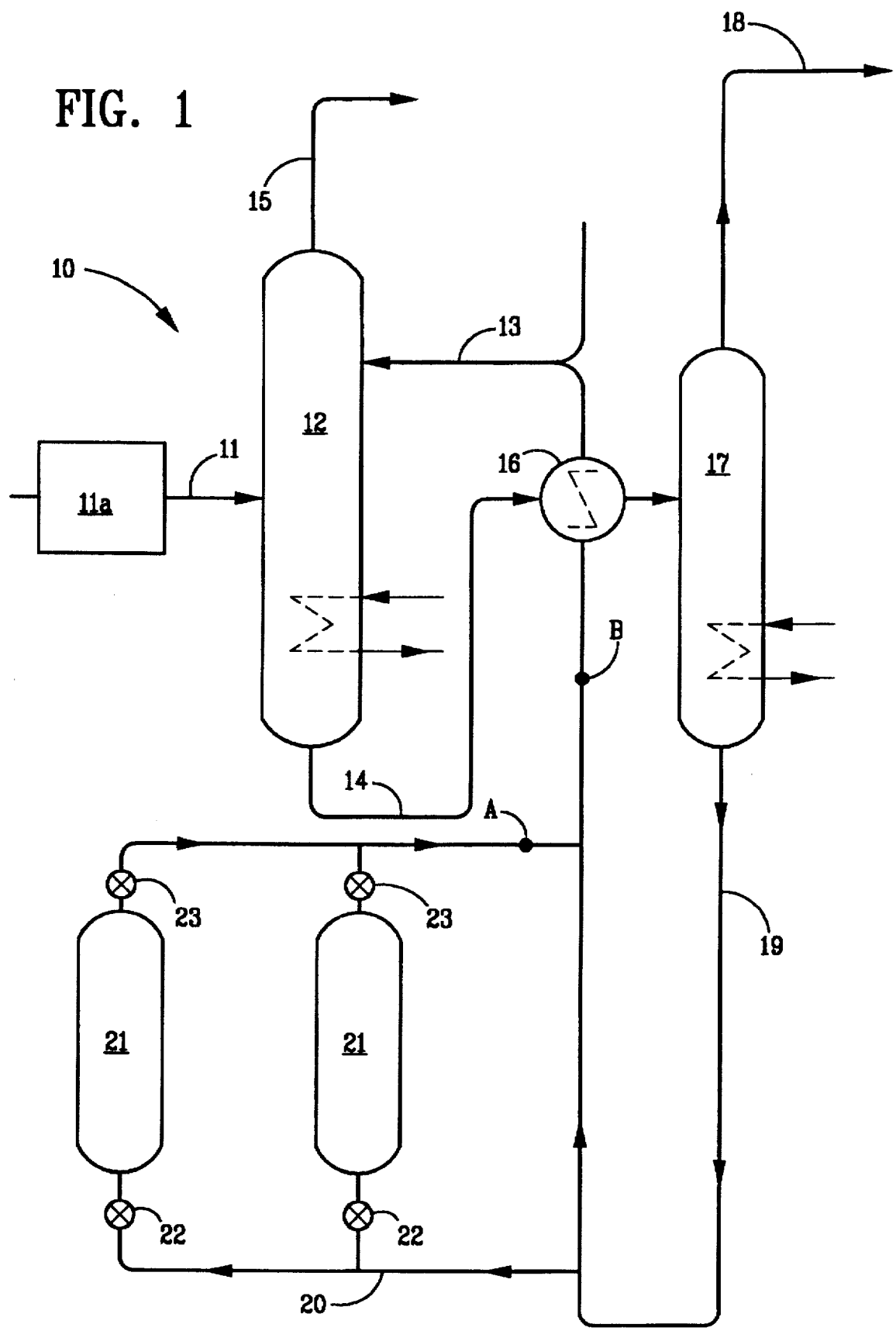
FIG. 1 is a schematical representation of a typical, prior art gas treatment process in which the present invention can be used to measure the efficiency of carbon filters to remove hydrocarbon from a regenerated solvent.

Referring now to the drawings, FIG. 1 schematically illustrates a typical "sour gas" solvent treatment process 10 wherein a stream of sour gas is fed through a line 11 into a high-pressure contactor vessel 12. As will be understood by those skilled in the art, "sour gas" is one which is comprised of a wide range of hydrocarbons (i.e. methane, hexane, dodecane, etc.) which also include a substantial amount of "acid gases" (i.e. hydrogen sulfide ($H_2S$), carbon dioxide ($CO_2$), etc.). The gas stream must be treated to remove or reduce the acid gases to acceptable levels (e.g. from 4–6% $H_2S$ to less than 0002% and from 3–5% $CO_2$ to less than 3%) before the gas can be sent to market. Also, as will be understood, the gas stream can be pretreated (e.g. passing it through a silica gel absorber 11a) before it is fed to contactor vessel 12.

Contactor vessel 12 is typically bubble-tray tower (e.g. 52 feet high) which has a plurality of horizontal trays (not shown) spaced therein wherein the incoming stream 11 of sour gas flows upward while a solvent flows into vessel 12 near its top and flows downward. Vessel 12 is normally operated at about 1000 psig and 100° F. The solvent is one which will absorb the acid gases from the hydrocarbon gas stream upon contact and will carry the acid gases out the bottom of vessel 12 through outlet 14. The solvent is preferably a liquid amine mixture (e.g. "Sulfinol", commercially-available from Shell Oil Company, which is basically comprised of approximately 50% methyldiethanolamine (MDEA), 25% cyclo-tetramethylene sulfone (sulfolane), and 25% water).

The MDEA absorbs $H_2S$ and $CO_2$ while the sulfolane absorbs the $H_2S$. The "rich" solvent (i.e. solvent plus absorbed acid gases) is passed through outlet line 14, through a heat exchanger 16, and into solvent regeneration vessel 17 wherein the operating pressure is reduced to about 15 psig and the temperature is increased to about 250° F. This breaks the weak bond between the solvent and the acid gases so that the acid gases are readily separated from the solvent. Both the solvent absorption of the acid gases and the regeneration of the solvent as described above are well known in this art.

The separated acid gases then pass from the top of regenerator 17 and through line 18 for further processing and handling; e.g. to a Claus process where sulfur is recovered from the $H_2S$ gas, as is also known in the art. The regenerated solvent passes from the bottom of regenerator vessel 17 through line 19, through heat exchanger 16 where it gives up heat to the rich solvent in line 14, and back into contactor vessel 12 through line 13 where it again absorbs acid gases from the sour gas stream and the process is repeated.

Unfortunately, however, some of the hydrocarbons (e.g. $C_5$+) in the sour gas stream are also soluble in the solvent. A small portion of these hydrocarbons are absorbed into the rich solvent and are carried therewith from the contactor 12 but are not readily separated along with the acid gases during regeneration of the solvent. The buildup of these hydrocarbons in the recycled, regenerated solvent will continue until the volume of hydrocarbons in the solvent exceeds an unacceptable level (e.g. 1.5% by volume) whereupon the amines in the solvent becomes emulsive and will begin to "foam", thereby forming bubbles which, in turn, trap acid gas therein.

These bubbles build up on the trays within the contactor 12 until they break, thereby releasing acid gas back into the processed or sales gas stream 15 which is being drawn from the top of contactor 12. When this happens, contactor 12 loses its effectiveness and acid gas ($H_2S$) detectors (not shown) on sales gas line 15 sense the increase in acid gas and may shut the process down thereby leading to expensive downtime and delay.

It has been found that the hydrocarbon buildup in the regenerated solvent can be controlled by passing a relatively small side or slip stream 20 of the regenerated solvent through a carbon filter(s) 21. For example, a side stream 20 of about 75–80 gallons from a main stream of 350 gallons in line 19 is usually sufficient to control the buildup of hydrocarbons in the regenerated solvent. While only one filter unit 21 can be used, preferably at least two units are connected in parallel so that by properly manipulating inlet valves 22 and outlet valves 23, the side stream can be switched between units when one filter becomes saturated. This allows continuous filtering of the side stream even while the carbon is being changed. Also, in some instances, as pointed out above, the carbon filter(s) 21 are used in conjunction with other known hydrocarbon extraction means (e.g. silica gel absorption beds 11a).

The carbon filter 21 substantially reduces the amounts of hydrocarbons in the regenerated solvent thereby controlling the amount of hydrocarbons which return to contactor 12. However, as with all filters, filter(s) 21 eventually becomes saturated to a level whereat the absorption capacity of the filter is no longer effective to control the hydrocarbon buildup in the solvent. That is, it has been found that when the level of hydrocarbons in the returned, regenerated solvent approaches 2% by volume, foaming will occur in contactor vessel 12.

Previously, the saturation of the carbon filter was not closely monitored and was only of concern when the diffential pressure across the filter substantially increased. This indicated that the filter was likely becoming plugged and hence, was saturated with hydrocarbons. The carbon was then changed out, but by this time, (1) foaming may have already started to occur in the contactor vessel; (2) excessive acid gases have started to show up in the sales gas; and/or (3) excessive $SO_2$ may have been detected in the flue stack emissions, any of which would likely require shut down of the gas treatment process. Such shut downs obviously adversely effect the overall economics of the gas treatment process.

As will be recognized by those skilled in this art, the basic gas treatment process described to this point is generally well known in the art. In accordance with the present invention, a method is provided wherein the hydrocarbon saturation of carbon filter(s) 21 can be monitored on a routine basis. This allows the carbon filter to be changed before the saturation level of the filter reaches that at which it no longer will sufficiently absorb hydrocarbons from the regenerated solvent to prevent foaming and/or other negative side-effects from occurring in the process.

Basically, a sample point A is provided just downstream of the outlet of the filter(s) 21 from which a sample of the regenerated solvent can be taken after it has passed through filter 21. This sample will indicate the degree of saturation of the filter(s). Also, a second sample point B may be provided in return line 19 downstream of the point where side stream 20 is rejoined with line 19 from which the total hydrocarbon contamination of the recycled solvent can be determined.

A sample from either point A and/or B can be taken on a regular schedule (e.g. daily) and is passed through a gas chromatograph (GC). The results from the GC are then processed and then analyzed using a special calibration table which previously has been compiled from known reference sample. When this analysis indicates that the hydrocarbon saturation in a sample taken from either sample point is approaching an unacceptable level (e.g. 1.5% by volume), the carbon in filter(s) 21 is changed and the process is resumed. As shown, flow can easily be switched from the saturated filter 21 to the other filter without stopping the slip stream 20.

More specifically, the gas chromatography method of the present invention differs from known GC methods in that it does not require an internal standard to be added to each sample before the sample is run through the GC and further, it does not require that the volume of the sample be accurately measured as is the case with most prior GC operations.

In carrying out the present method, a special calibration table is first compiled by passing a known test sample through the GC. The test sample is comprised of (a) a known volume of the particular solvent used in process and (b) a known volume of the actual hydrocarbons which will be present in the particular hydrocarbon gas stream to be treated. The resulting chromatogram is analyzed and the "reduction factors" (RF) for each of the hydrocarbon components in the test sample are calculated either by using standard GC techniques or, preferably, by using a known and well accepted theoretical relationship. The RF(s) for the solvent is determined by manual analysis as will be discussed below. Next, an actual sample is taken from point A or B and is run through the GC. The RF from the calibration table is then used to determine the actual amounts of hydrocarbons in the sample. To further explain the present invention, the following specific example is set forth.

First a measured amount (1% by volume) of a mixture of known hydrocarbons (e.g. $C_1-C_{10}$) was mixed with a measured amount (99% by volume) of solvent (e.g. organic amine comprising 66% Sulfolane and 33% MDEA. This test mixture was then passed through a standard gas chromatograph, e.g. "Hewlett Packard" GC HP5890 equipped with a liquid autosampler and a flame ionization detector. The carrier gas can be either helium or hydrogen. The GC included a capillary GC column, e.g. "Supelco" methyl silicate, 60M×0.32MM, fused silica capillary column, 1.0 micron film thickness or equivalent. The GC had an inlet temperature of 250° C., a detector temperature of 200° C., and an initial column temperature of 40° C.

As will be understood in this art, RFs are used in gas chromatography to translate the area counts produced by a particular material on the trace of a chromatogram into numbers that reflect the true amount of that respective material in a test sample. Theoretical RFs for the analysis of hydrocarbon streams in gas chromatography has been used for several years and is a common practice in the petroleum industry. One widely accepted relationship for calculating RFs is:

$RF=[(12 \times C)+H]/[12 \times C \times 1.33467]$ wherein

C=number of carbon atoms

H=number of hydrogen atoms

For example, for Cyclohexane ($C_6H_{12}$)

$RF=[(12 \times 6)+12]/[12 \times 6 \times 1.33467]=0.8741$

Figure 2:
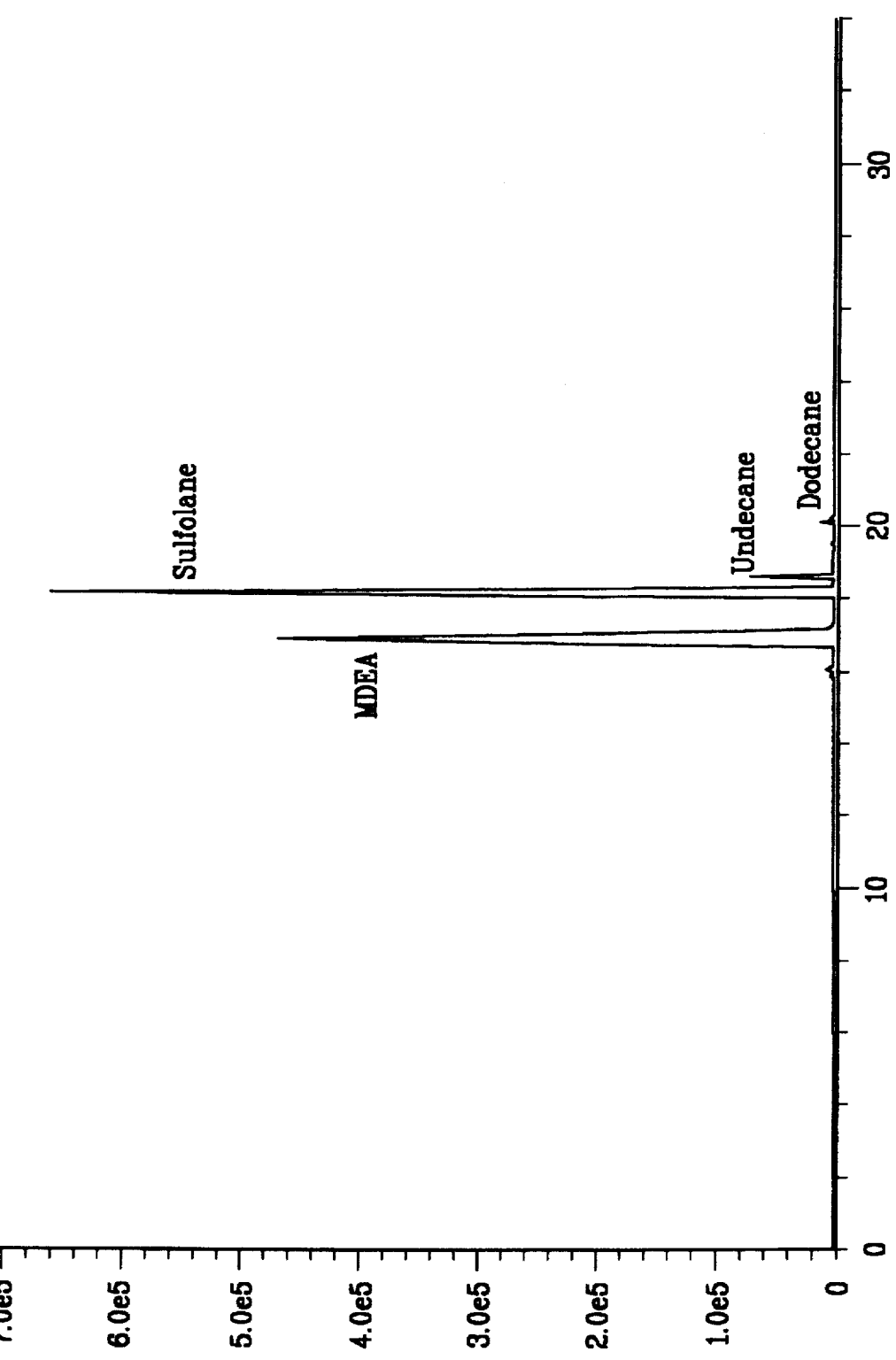
FIG. 2 is a typical gas chromatogram representative of a sample of a particular, regenerated solvent after it has passed through a carbon filter.

The RFs for each of the known hydrocarbon components of the gas stream to be processed was calculated as described above. Since the known amount and the composition of a hydrocarbon mixture were mixed with a known amount of the organic amine solvent, a RF for the amine solvent could be established by manually inputting a value into the calibration table and then adjusting that value until it accurately reflects the known composition of the entire mixture. For example, for the mixture of 66% Sulfolane, 33% MDEA, and 1% known hydrocarbons, the RFs for Sulfolane and MDEA were determined to be 2.7227 and 3.7086, respectively. When these RFs were checked against those derived from other known mixtures of the same basic components, the results proved to be reproducible within an accuracy of ±1%. The results were then compiled into the following special calibration table (Table I) which is representative of the special calibration tables used in the present invention:

produce a chromatogram such as that shown in FIG. 2. While only the areas under those "peaks" which are representative of the MDEA, Sulfolane, undecane, and dodecane components are clearly evident on the trace, it will be recognized that the much smaller peaks representing the other hydrocarbon components are readily discernable by standard GC analysis techniques.

The areas under these peaks (i.e. area counts) are then multiplied by the respective RFs taken from the special calibration table and the results thereof were normalized to provide the relative amounts (i.e. percentage) of each component in the tested sample. An example of such an analysis for a chromatogram such as that of FIG. 2 is shown in the following table (Table II):

TABLE I

| PEAK NO. | REF. TIME | MOLE % | RF | | HC |
|---|---|---|---|---|---|
| 1 | 4.452 | 0.02 | 0.999 | | C1 METHANE |
| 2 | 4.606 | 0.02 | 0.9366 | | C2 ETHANE |
| 3 | 4.900 | 0.02 | 0.9157 | | C3 PROPANE |
| 4 | 5.142 | 0.02 | 0.9366 | | C4 ISOBUTANE |
| 5 | 5.258 | 0.02 | 0.9366 | | C4 N-BUTANE |
| 6 | 5.954 | 0.02 | 0.8991 | | C5 NEOPENTANE |
| 7 | 6.005 | 0.02 | 0.8991 | | C5 ISOPENTANE |
| 8 | 6.587 | 0.02 | 0.8991 | | C5 N-PENTANE |
| 9 | 7.055 | 0.02 | 0.8741 | | C2-PENTENE |
| 10 | 7.292 | 0.02 | 0.8949 | | 2,2 DIMETHYLBUTANE |
| 11 | 7.719 | 0.02 | 0.8741 | | CYCLOPENTANE |
| 12 | 7.810 | 0.02 | 0.8991 | | 2 METHYL PENTANE |
| 13 | 8.617 | 0.02 | 0.949 | | 3-METHYL PENTANE |
| 14 | 8.828 | 0.02 | 0.8949 | | C6 N-HEXANE |
| 15 | 9.017 | 0.02 | 0.892 | | 2,2 DIMETHYL PENTANE |
| 16 | 9.441 | 0.02 | 0.8741 | | CYCLOHEXANE |
| 17 | 9.617 | 0.02 | 0.874 | | METHYLCYCLOPENTANE |
| 18 | 9.740 | 0.02 | 0.8117 | | C6 BENZENE |
| 19 | 10.483 | 0.02 | 0.892 | | 2-METHYLHEXANE |
| 20 | 10.585 | 0.02 | 0.892 | | 2,3 DIMETHYL PENTANE |
| 21 | 10.771 | 0.02 | 0.8563 | | 1,1 DIMETHYLCYCLOPEN ... |
| 22 | 10.828 | 0.02 | 0.8563 | | 1,T-3 DIMETHYLCYCLOP ... |
| 23 | 10.950 | 0.02 | 0.8563 | | 1,C2 DIMETHYLCYCLOPE ... |
| 24 | 11.000 | 0.02 | 0.8563 | | 1,T-2,DIMETHYLCYCLOP ... |
| 25 | 11.050 | 0.02 | 0.892 | | N-HEPTANE |
| 26 | 11.126 | 0.02 | 0.8741 | | METHYLCYCLOHEXANE |
| 27 | 11.169 | 0.02 | 0.8741 | | TOLUENE |
| 28 | 12.100 | 0.02 | 0.8206 | | ETHYLBENZENE |
| 29 | 12.300 | 0.02 | 0.8273 | | PARA/META XYLENE |
| 30 | 12.500 | 0.02 | 0.8273 | | O-XYLENE |
| 31 | 12.700 | 0.02 | 0.8602 | | 4 METHYLNONANE |
| 32 | 12.900 | 0.02 | 0.8325 | | ISOPROPYLBENZENE |
| 33 | 13.000 | 0.02 | 0.8325 | | 3,3 DIMETHYLHEPTANE |
| 34 | 14.361 | 0.02 | 0.8325 | | PARA ETHYL TOLUENE |
| 35 | 15.000 | 0.02 | 0.8325 | | META ETHYL TOLUENE |
| 36 | 15.362 | 0.02 | 0.8602 | | 3 ETHYLNONANE |
| 37 | 15.556 | 0.02 | 0.8602 | | ISOBUTYLCYCLOBENZENE |
| 38 | 16.051 | 0.02 | 0.8602 | | METHYL 3-ISOPROPYL B ... |
| 39 | 16.305 | 0.02 | 0.8602 | | 1METHYL, 4ISOPROPYL B ... |
| 40 | 16.448 | 0.02 | 0.8622 | | 1METHYL, 2ISOPROPYL B ... |
| 41 | 16.925 | 66.231 | 3.7086 | Ref | MDEA |
| 42 | 17.265 | 0.02 | 0.8866 | | DECANE |
| 43 | 18.075 | 33.113 | 2.7227 | Ref | SULFOLANE |
| 44 | 18.212 | 0.02 | 0.8855 | | UNDECANE |
| 45 | 19.664 | 0.02 | 0.8845 | | DODECANE |

After compiling the special calibration table for a particular gas treating process, an actual sample was taken from the gas treatment process at point A (i.e. after the regenerated solvent (Sulfinol) had passed through the carbon filter 21). A single drop of this sample, which does not have to be accurately measured, was added to a GC autosampler vial which, in turn, was then topped off with demineralized or distilled water. This prepared sample, which again does have to be accurately measured, was passed through the GC to

TABLE II

| REF. TIME | AREA | PEAK WIDTH | PEAK AMOUNT | NAME |
|---|---|---|---|---|
| 5.374 | 400 | 0.037 | 0.00104 | C4 N-BUTANE |
| 5.955 | 1361 | 0.033 | 0.00338 | C5 NEOPENTANE |
| 10.259 | 257 | 0.035 | 0.000635 | 2-METHYLHEXANE |

TABLE II-continued

| REF. TIME | AREA | PEAK WIDTH | PEAK AMOUNT | NAME |
|---|---|---|---|---|
| 11.141 | 2706 | 0.037 | 0.00668 | N-HEPTANE |
| 11.299 | 1867 | 0.087 | 0.00452 | TOLUENE |
| 14.44 | 752 | 0.029 | 0.00173 | PARA ETHYL TOLUENE |
| 15.449 | 612 | 0.044 | 0.00146 | 3 ETHYLNONANE |
| 15.632 | 747 | 0.054 | 0.00178 | ISOBUTYL-CYCLOBENZENE |
| 16.174 | 1026 | 0.042 | 0.00244 | METHYL 3-ISOPROPYL BENZENE |
| 16.372 | 2509 | 0.084 | 0.00597 | 1METHYL,4ISOPROPYL BENZENE |
| 17.047 | 6672906 | 0 | 68.463 | MDEA |
| 17.502 | 6703 | 0.054 | 0.0164 | DECANE |
| 18.188 | 4132936 | 0.081 | 31.131 | SULFOLANE |
| 18.503 | 126274 | 0.025 | 0.309 | UNDECANE |
| 20.013 | 20852 | 0.029 | 0.051 | DODECANE |

It can be seen that the saturation of the carbon filters can be monitored at any time during the gas treatment process by merely taking a sample from point A or the total contamination of the recycled solvent can be monitored by taking a sample from point B and passing it through a GC. This can be done by actually drawing the sample and then manually feeding it into the GC or an automatic sampling system can be used wherein samples are automatically taken from point A and/or B and then supplied to an on-line GC such as those which are commercially-available from various suppliers, e.g. Hewlett Packard; Perkin-Elmer, etc..

The resulting chromatogram is then analyzed and processed using the RFs from the special calibration table to determine the amount of hydrocarbons present in the sample, hence in the recycled solvent. When the total amount of the hydrocarbons in the tested, recycled solvent approaches the unacceptable level (e.g. 1.5%), the carbon can be changed well before the process ever experiences any adverse side-effects.

Also, by using the special calibration table of RFs compiled in accordance with the present invention, the use of internal standards and elaborate calibration and sample preparation and the need for careful measurements are eliminated. This allows the saturation of the carbon filter(s) to be monitored at any given time with minimum effort and without the need for an experienced GC operator.

What is claimed is:

1. A method for treating a sour hydrocarbon gas stream, said method comprising:

contacting said sour hydrocarbon gas stream with a solvent to remove acid gases from said sour gas stream;

regenerating said solvent by removing said acid gases from said solvent to form a regenerated solvent;

passing at least a portion of said regenerated solvent through a carbon filter to remove hydrocarbons from said solvent and form a regenerated, filtered solvent, said hydrocarbons having been absorbed from said sour gas stream along with said acid gases;

recycling said regenerated, filtered solvent for use in further removing acid gases from said sour gas stream;

determining the absorption efficiency of said carbon filter for removing said hydrocarbons from said regenerated solvent on a routine basis by periodically taking a sample of said regenerated solvent after it has passed through said carbon filter; and changing said carbon filter after the amount of hydrocarbons remaining in said regenerated, filtered solvent after it has passed through said carbon filter approaches an unacceptable level.

2. The method of claim 1 wherein said acid gases are hydrogen sulfide and/or carbon dioxide and the solvent comprises an organic amine.

3. The method of claim 2 wherein said solvent is comprised of the organic amine and sulfolane (cyclotetramethylene sulfone).

4. The method of claim 2 wherein said absorption efficiency of said carbon filter is determined by:

taking a sample of said regenerated solvent after it has passed through said carbon filter;

passing said sample through a gas chromatograph to measure the relative area counts of both the known hydrocarbons and the solvent in said filtered, regenerated solvent; and converting said relative area counts measured by said gas chromatograph into respective amounts of said hydrocarbons and solvent by using predetermined, respective references values for said hydrocarbons and said solvent thereby determining the total amount of hydrocarbons in said regenerated solvent after said solvent has passed through said carbon filter and hence determining the efficiency of said filter to absorb hydrocarbons at the time said sample was taken.

5. The method of claim 4 wherein said reference values are the Reduction Factors for said respective hydrocarbons and said solvent.

6. The method of claim 5 where said Reduction Factors (RF) for said respective hydrocarbons are calculated in accordance with the following relationship:

RF=[(12×C)+H]/[12×C×1.33467] wherein

C=number of carbon atoms

H=number of hydrogen atoms.

7. The method of claim 2 wherein said unacceptable level of hydrocarbons in said regenerated, filtered solvent is equal to about 1.5% by volume, of the filtered regenerated solvent.

8. In a method for treating a hydrocarbon gas stream by (a) removing acid gases from said gas stream by contacting said stream with a solvent; (b) regenerating said solvent by removing said acid gases from said solvent to form regenerated solvent; (c) passing at least a portion of said regenerated solvent through a carbon filter to remove hydrocarbons from said solvent and form regenerated, filtered solvent; and (d) recycling said regenerated, filtered solvent for use in removing said acid gases from said hydrocarbon stream; the improvement comprising:

a method for determining the efficiency of said carbon filter for absorbing said hydrocarbons from said regenerated solvent; said method comprising:

taking a sample of said regenerated, filtered solvent after it has passed through said carbon filter;

passing said sample through a gas chromatograph to measure the relative area counts of both said hydrocarbons and said solvent in said regenerated, filtered, solvent; and converting said relative area counts measured by said gas chromatograph into respective amounts of said hydrocarbons and solvent by using predetermined, respective reference values for said hydrocarbons and said solvent thereby determining the total amount of hydrocarbons in said regenerated, filtered solvent after said solvent has passed through said carbon filter and hence determining the efficiency of said filter to absorb said hydrocarbons at the time said sample was taken.

9. The method of claim 8 wherein said acid gases are hydrogen sulfide and carbon dioxide and the solvent comprises an organic amine.

10. The method of claim 9 wherein said solvent comprises the organic amine and sulfolane (cyclo-tetramethylene sulfone).

11. The method of claim 8 wherein said reference values are the Reduction Factors for said hydrocarbons and said solvent.

12. The method of claim 11 where said Reduction Factors (RF) for said respective hydrocarbons are calculated in accordance with the following relationship:

$RF = [(12 \times C) + H]/[12 \times C \times 1.33467]$ wherein

C = number of carbon atoms

H = number of hydrogen atoms.

13. A method for determining the absorption efficiency of a carbon filter in removing hydrocarbons from a solvent; said method comprising:

taking a sample of said solvent after it has passed through said carbon filter to form a filtered solvent;

passing said sample through a gas chromatograph to measure the relative area counts of both the hydrocarbons and the solvent in said filtered solvent; and converting said relative area counts measured by said gas chromatograph into respective amounts of said hydrocarbons and solvent by using predetermined, respective reference values for said hydrocarbons and said solvent thereby determining the total amount of hydrocarbons in said regenerated solvent after said solvent has passed through said carbon filter and hence determining the efficiency of said filter to absorb said hydrocarbons at the time said sample was taken.

14. The method of claim 13 wherein said solvent comprises an organic amine.

15. The method of claim 13 wherein said reference values are the Reduction Factors for said respective hydrocarbons and said solvent.

16. The method of claim 15 where said Reduction Factors (RF) for said respective hydrocarbons are calculated in accordance with the following relationship:

$RF = [(12 \times C) + H]/[12 \times C \times 1.33467]$ wherein

C = number of carbon atoms

H = number of hydrogen atoms.

\* \* \* \* \*